United States Patent
Marino et al.

(10) Patent No.: US 7,144,410 B2
(45) Date of Patent: *Dec. 5, 2006

(54) ASD CLOSURE DEVICE WITH SELF CENTERING ARM NETWORK

(75) Inventors: Joseph A. Marino, Apple Valley, MN (US); Michael P. Corcoran, Woodbury, MN (US)

(73) Assignee: Cardia Inc., Eagan, MN (US)

( * ) Notice: Subject to any disclaimer, the term of this patent is extended or adjusted under 35 U.S.C. 154(b) by 505 days.

This patent is subject to a terminal disclaimer.

(21) Appl. No.: 10/666,081

(22) Filed: Sep. 18, 2003

(65) Prior Publication Data

US 2005/0065547 A1    Mar. 24, 2005

(51) Int. Cl.
*A61B 17/08* (2006.01)
*A61B 17/00* (2006.01)

(52) U.S. Cl. ...................... 606/213; 128/887

(58) Field of Classification Search ........ 606/151–158, 606/213, 200; 128/887; 623/2.2, 2.23–2.25
See application file for complete search history.

(56) References Cited

U.S. PATENT DOCUMENTS

| | | | |
|---|---|---|---|
| 3,874,388 A | 4/1975 | King et al. | |
| 4,007,743 A | 2/1977 | Blake | |
| 4,917,089 A | 4/1990 | Sideris | |
| 5,108,420 A | 4/1992 | Marks | |
| 5,171,259 A | 12/1992 | Inoue | |
| 5,284,488 A | 2/1994 | Sideris | |
| 5,334,137 A | 8/1994 | Freeman | |
| 5,334,217 A | 8/1994 | Das | |
| 5,350,399 A * | 9/1994 | Erlebacher et al. | ......... 606/213 |
| 5,382,260 A | 1/1995 | Dormandy, Jr. et al. | |
| 5,397,331 A | 3/1995 | Himpens et al. | |
| 5,425,744 A | 6/1995 | Fagain et al. | |
| 5,433,727 A | 7/1995 | Sideris | |
| 5,451,235 A | 9/1995 | Lock et al. | |
| 5,601,595 A * | 2/1997 | Smith | .......................... 606/200 |
| 5,634,936 A | 6/1997 | Linden et al. | |
| 5,649,950 A | 7/1997 | Bourne et al. | |
| 5,702,421 A | 12/1997 | Schneidt | |
| 5,709,707 A | 1/1998 | Lock et al. | |
| 5,725,552 A | 3/1998 | Kotula et al. | |
| 5,741,297 A | 4/1998 | Simon | |
| 5,853,422 A * | 12/1998 | Huebsch et al. | ............ 606/213 |
| 5,904,703 A | 5/1999 | Gilson | |
| 5,944,738 A * | 8/1999 | Amplatz et al. | ............ 606/213 |

(Continued)

FOREIGN PATENT DOCUMENTS

DE          233 303 A1    2/1986

(Continued)

*Primary Examiner*—Glenn Dawson
*Assistant Examiner*—Kathleen Sonnett
(74) *Attorney, Agent, or Firm*—Kinney & Lange, P.A.

(57) ABSTRACT

The present invention provides an occluder with a self centering system that keeps the occluder properly centered in a defect which allows the center of the occluder to remain properly positioned within the defect so that the left and right sides cover the entire defect which reduces the chance of blood shunting through the defect and increases the effectiveness of the occluder. The self centering system is comprised of a series of arms that provide tension to hold the right and left sides in place. The arms are shaped to provide a flexible intermediate zone comprising a left and a right conical shaped network, wherein each network extends from the right and left sides and narrows at the center section. The flexible intermediate zone centers the occluder and helps to hold it in place.

20 Claims, 6 Drawing Sheets

U.S. PATENT DOCUMENTS

| | | |
|---|---|---|
| 6,024,756 A | 2/2000 | Huebsch et al. |
| 6,174,322 B1* | 1/2001 | Schneidt .................... 606/213 |
| 6,206,907 B1* | 3/2001 | Marino et al. ............. 606/215 |
| 6,379,368 B1* | 4/2002 | Corcoran et al. .......... 606/153 |
| 6,656,206 B1* | 12/2003 | Corcoran et al. .......... 606/213 |
| 6,911,037 B1* | 6/2005 | Gainor et al. ............... 606/213 |
| 6,960,220 B1* | 11/2005 | Marino et al. ............. 606/153 |
| 6,960,224 B1* | 11/2005 | Marino et al. ............. 606/215 |
| 2004/0143291 A1* | 7/2004 | Corcoran et al. .......... 606/213 |
| 2005/0065546 A1* | 3/2005 | Corcoran et al. .......... 606/213 |

FOREIGN PATENT DOCUMENTS

| | | |
|---|---|---|
| DE | 4222291 | 1/1994 |
| EP | 0 362 113 A1 | 4/1990 |
| EP | 0 541 063 A2 | 5/1993 |
| EP | 0 541 063 A3 | 5/1993 |
| EP | 0 541 063 B1 | 9/1998 |
| GB | 2 269 321 A | 2/1994 |

* cited by examiner

ASD CLOSURE DEVICE WITH SELF CENTERING ARM NETWORK

BACKGROUND OF THE INVENTION

This invention relates to an occlusion device for the closure of physical apertures, such as vascular or septal apertures. More specifically, this invention relates to an occlusion device for the heart that centers itself in the defect to ensure that the defect is properly sealed.

The heart is generally comprised of four chambers: the left and right atrium, and the left and right ventricle. Separating the left and right sides of the heart are two walls, or septa. The wall between the two atria is the interatrial septum, and the wall between the two ventricles is the interventricular septum. There are several defects which can affect the septa of both children and adults, including patent ductus arteriosus, patent foramen ovale, atrial septal defects (ASDs), and ventricular septal defects (VSDs). Although the causes and physical aspects of these defects vary by type, each of these defects is generally an aperture, flap, or hole, in the septum which allows blood to shunt between chambers in the heart where there is no blood flow in a normal, healthy heart. This abnormal shunt can cause a variety of health problems.

Normally, permanently repairing certain cardiac defects in adults and children requires open heart surgery, which is a risky, painful, and expensive procedure. Surgery for closure of a heart defect is major heart surgery, which requires the patient to undergo general anesthesia and opening of the chest cavity. The patient must spend several days in the hospital and thereafter may take several weeks to be able to return to normal levels of activity.

To avoid the risks and discomfort associated with open heart surgery, modern occlusion devices have been developed that are small, implantable devices capable of being delivered to the heart through a catheter. These devices effectively seal the defect but do not require surgery. Rather than surgery, a catheter inserted into a major blood vessel allows an occlusion device to be deployed at the defect by moving the device through a catheter to the treatment site. This procedure is performed in a cardiac cathlab and avoids the risks and pain associated with open heart surgery.

These modern occlusion devices can repair a wide range of cardiac defects, including patent foramen ovale, patent ductus arteriosus, atrial septal defects, ventricular septal defects, and may occlude other cardiac and non-cardiac apertures. One form of an occlusion device generally has a left side, a right side, and a center section. Once the occluder is deployed, the occluder's center section extends through the center of the defect. The left and right sides occlude the aperture on the respective sides of the patient's septum.

As mentioned, several types of septal defects exist. In addition, the size of each defect varies from patient to patient. If the defect is large, the center section of the occluder must remain in the center of the defect so that the left and right sides of the occluder cover the entire aperture. If the occlusion device moves or is not properly centered in the defect, the occlusion device may not properly occlude the defect. If the defect is not properly occluded, blood will continue to shunt through the defect, which lessens the effectiveness of the occluder.

Thus, there is a need in the art for an occlusion device which has a centering system to keep the device properly centered in the defect.

BRIEF SUMMARY OF THE INVENTION

The present invention provides an occluder with a self centering system that keeps the occluder properly centered in a defect. The self centering system allows the center of the occluder to remain properly positioned within the defect so that the left and right sides cover the entire defect, which reduces the chance of blood shunting through the defect and increases the effectiveness of the occluder. The self centering system is comprised of a series of arms that provide tension to hold the right and left sides in place. The arms are shaped to provide a flexible intermediate zone comprising a left and a right conical shaped network, wherein each network extends from the right and left sides and narrows at the center section. The flexible intermediate zone centers the occluder and helps to hold it in place.

DETAILED DESCRIPTION

Figure 1:
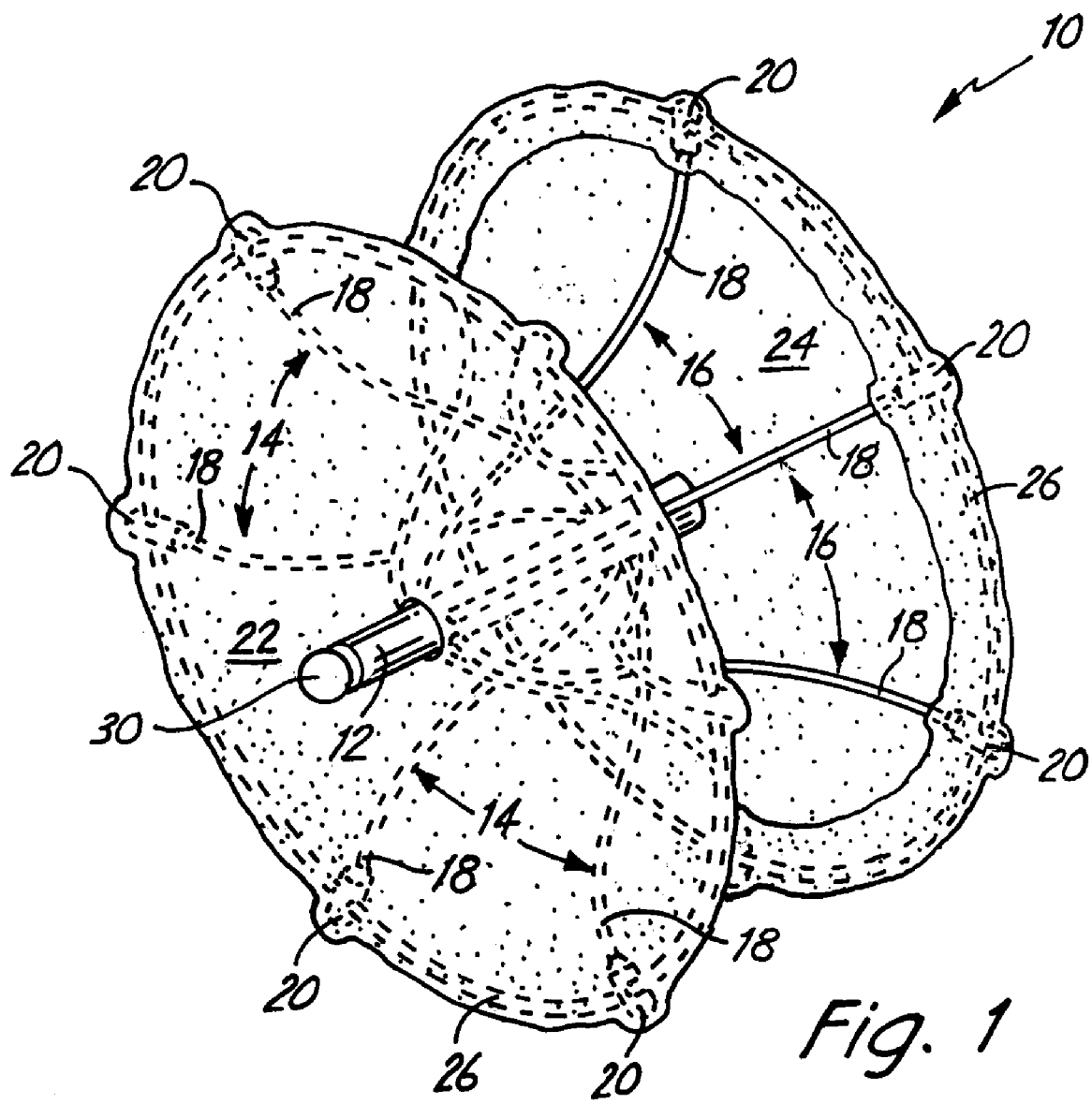
FIG. 1 is a perspective view of an occlusion device.

FIG. 1 is a perspective view of an occlusion device 10. The occlusion device 10 comprises a center post 12, a right set of arms 14, a left set of arms 16, individual wire arms 18 which make up the left and right sets 14, 16, end caps 20, a right sheet 22, a left sheet 24, and two wire hoops 26. The right set of arms 14 is connected to the center post 12 and comprises the six wire arms 18 which are capped with the end caps 20. The hoops 26 surround the perimeter of the right and left sheets 22, 24 and pass through holes 28 in the end caps 20. A grasping knob 30 is located near the tip of the center post 12. Both sets of arms 14, 16 are located on the inner sides of the sheets 20, 22.

The sheets 22, 24 are connected to the device 10 at the hoops 26. The sheets 22, 24 may attach to the hoops 26 by folding each sheet 24, 26 over the perimeter of the hoop 26 and securing the sheets 22, 24 in place. A variety of securing methods may be used such as suturing, heat treating, or laminating. Methods of attaching the sheets 22, 24 to the hoops 26 are described more fully in FIGS. 8 and 9.

The sheets 22, 24 are preferably formed of a medical grade polymer. One suitable material is DACRON®. Preferably, the sheets 22, 24 are formed of a high density polyvinyl alcohol (PVA) foam, such as that offered under the trademark IVALON®. To minimize the chance of the device 10 causing a blood clot, the sheets 22, 24 may be treated with a thrombosis-inhibiting material. One such suitable material is heparin.

The size of the sheets 22, 24 may vary to accommodate various sizes of defects. In some instances, it may be desirable to form the sheets 22, 24 so that they are not both the same size. For instance, one sheet and its associated set of arms can be made smaller than the corresponding sheet and its associated set of arms. This is particularly useful in situations where the occlusion device 10 is to be placed at a location in the heart which is close to other nearby cardiac structures. Making the sheets 22, 24 different sizes may assist in providing optimal occlusion of a defect, without affecting other structures of the heart which may be nearby.

Figure 2:
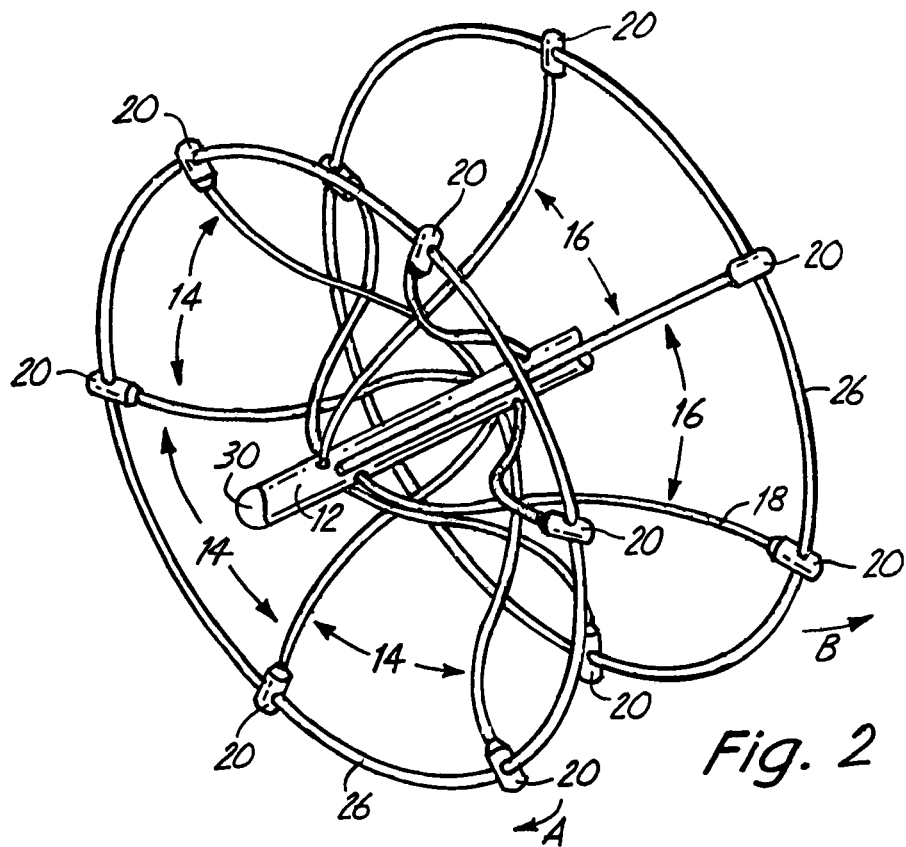
FIG. 2 is a side perspective view of the right side of an occlusion device frame.

FIG. 2 is a perspective view of the occlusion device 10 without the sheets 22, 24 attached so that the frame of the device 10 may be more easily observed. Shown in FIG. 2 is the center post 12, the right set of arms 14, the left set of arms 16, end caps 20, two wire hoops 26 and the grasping knob 30. The left and right sets of arms 14, 16 are comprised of six arms 18 which are capped by end caps 20.

The right and left sets of arms 14, 16 are connected to the center post 12. The center post 12 has holes drilled into the center post 12 on both ends, or sides. One method of connecting the right and left sets of arms 14, 16 to the post 12 is to provide the center post 12 with drill holes through which the right and left sets of arms 14, 16 pass. When connected to the center post 12 using holes drilled through the center post 12, the right and left sets of arms 14, 16 may be formed of three wires. The three wires create the six arms 18 because the post 12 divides each wire into two arms 18 when the wire passes through the center post 12. The end caps 20, located at the distal ends of the arms 18, are rounded to minimize damage to the surrounding tissue when the device is deployed. The right set of arms 14 is threaded through holes located on the left side of the center post 12. Likewise, the left set of arms 16 is threaded through holes located on the right side of the center post 12. Each individual arm 18 of the left and right sets of arms 14, 16 is offset from adjacent arms 18 by 60°. In addition, the left and right sets of arms 14, 16 are offset from one another by 30°. This offsetting serves to more evenly space the arms 18 which helps to create a uniform seal around the defect.

The hoops 26 attach to the device at the end caps 22. The end caps 22 are provided with drilled holes through which the hoops 26 can pass for attachment. The hoops 26 are constructed of a single, heat shaped wire which is threaded through the end caps 22 and then secured. Methods of securing the ends of the hoops 26 are described more fully in FIGS. 7A and 7B.

The knob 30 on the center post 12 is configured to allow the device 10 to be grasped by a delivery device as the device 10 is guided through the catheter. However, the method of attachment to a delivery device is not so limited. The knob 30 may be modified as needed to attach to any delivery device. For instance, the knob 30 may be fitted with threads so that it may be screwed onto a delivery device that is outfitted with threads.

The device 10 is configured to be deployed through a catheter, and more specifically, the device 10 is constructed so that the sets of arms 14, 16 are easily collapsible about the center post 12 to allow the device 10 to be inserted through a catheter. Due to this construction, the device 10 can be folded such that the right set of arms 14 is folded in the axial direction A and the left set of arms 16 is folded in an opposite axial direction B, which allows the folded device 10 to fit into a small diameter catheter. The right and left sheets 22, 24 that attach to the sets of arms 14, 16 collapse as the sets of arms 14, 16 are folded. Likewise, the hoops 26 and the sheets 22, 24 are also flexible and are configured to collapse.

Once the device 10 is deployed across a defect in the heart, the sets of arms 14, 16, the hoops 26, and the sheets 22, 24 unfold to form a seal around each side of the defect. To ensure the device 10 returns to a shape capable of exerting enough pressure to seal the defect, the sets of arms 14, 16 are made of a suitable material capable of shape memory, such as nickel-titanium alloy, commonly called Nitinol. Nitinol is preferably used because it is commercially available, very elastic, non-corrosive and has a fatigue life greater than that of stainless steel. To further ensure that the sets of arms 14, 16 do not suffer from fatigue failures, one embodiment of the present invention comprises making the wire sets of arms 14, 16 of stranded wire or cables.

The wire arms 18 are preferably subjected to precise pre-shaping to give them a "shape memory." The pre-shaping can be done either by machining, heat treating, or both. The shape memory helps to hold the strands together when the arms 18 are formed of stranded wire or cable, and can be used to add pretension to the arms 18 so that they "remember" their shape even after undergoing a strong deformation when the device 10 is passed through a catheter. The end caps 22 may further serve to prevent potential unraveling of the arms 18 when the arms 18 are formed of stranded wire or cable.

The support hoops 26 are also made of a suitable material capable of shape memory, such as nickel-titanium alloy, like Nitinol. The hoops 26 maybe constructed of a single wire or stranded wire. The diameter of the wire that is used to form the support hoops 26 must be small enough so that the hoops 26 are flexible enough to collapse when the device 10 is being loaded or retrieved. However, the wire must be stiff enough to allow the hoops 26 to lie as flat as possible against the patient's septum to create an effective seal. Similar to the wire arms, the support hoops 26 may also be heat shaped or machine shaped so that they have shape memory to ensure that the hoops 26 resume the proper shape once the hoops 26 leave the catheter.

Another advantage of pre-shaping the hoops 26 using heat is to ensure that the hoops 26 are properly sized. If the hoops 26 are too large or too small for the device 10, the hoops 26 may cause the sheets 22, 24 to pucker. If the hoops 26 cause the sheets to pucker, the sheets 24, 26 cannot lie flat against the septum and therefore do not seal as effectively as if the sheets 22, 24 lie flat and hug the septum.

The support hoops 26 allow the device 10 to hug the tissue surrounding the defect to create a uniform seal around the opening of the defect, which improves the sealing capabilities of the occlusion device 10. The support hoops 26 further reduce the potential for increased pressure on surrounding tissue in any one area. More specifically, once deployed, the individual arms 18 that make up the sets of arms 14, 16 exert pressure on the hoops 26 and sheets 22, 24 to form a seal around the defect. Without the hoops 26, the highest points of pressure are the six or eight pressure points where the tips of the arms 18 may press against the tissue surrounding the defect. Given the uneven topography of the heart, some arms 18 put more pressure on surrounding tissue than others. Thus, instead of having six or eight pressure points, the support hoop 26 can more evenly distribute pressure around a continuous circle, decreasing the possibility that increased pressure will be exerted at any one contact point. By distributing pressure more evenly, the risk that one or more tips of the arms 18 will poke through the tissue, or poke through the defect, is greatly reduced.

The other parts of the stabilization device 10 are likewise formed of suitable materials. More specifically, the center posts 12, 14 may be formed of platinum-iridium and the end caps 22 may be formed of titanium. However, the invention is not limited to these materials and any suitably biocompatible material will suffice.

Though not immediately evident in FIGS. 1 and 2, the arms 18 vary slightly in length. This is so that when the device 10 is folded, the device 10 fits more easily into a catheter. To allow the device 10 to be retrievable, as well as ensure that the device 10 fits into as small a diameter catheter as possible, it is important to ensure that the arms 18 are not of a length that results in the end caps 22 clustering at the same location when loaded inside the catheter. If the end caps 22 all occur at the same location when the device 10 is inside the catheter, the device 10 may become too bulky to allow it to be easily moved through the catheter. In addition, though shown with six arms 18, the device 10 is not so limited. Rather, the device 10 may be comprised of four arms, or may be comprised of anywhere from five, six, eight, ten, or even more arms.

Another feature of the occlusion device 10 is that it is fully retrievable. In situations where the occlusion device 10 is not properly deployed and must be retrieved into a catheter, it is possible to withdraw the occlusion device 10 back into a catheter by grasping either the center section 12 or by grasping any one of the arms 16. As mentioned, it is important that the arms 18 are not of a length that results in the end caps 20 clustering at the same location. If the end caps 20 cluster at the same location when the device 10 is inside a catheter, the device 10 will become too bulky to easily move through a catheter. To make the device 10 retrievable, it is possible to vary the length of the upper arms 18 from the length of the lower arms 18 so that when the device 10 is retrieved, the end caps 20 on the upper arms 18 do not cluster at the same location as the end caps 20 on the lower arms 18.

Figure 3:
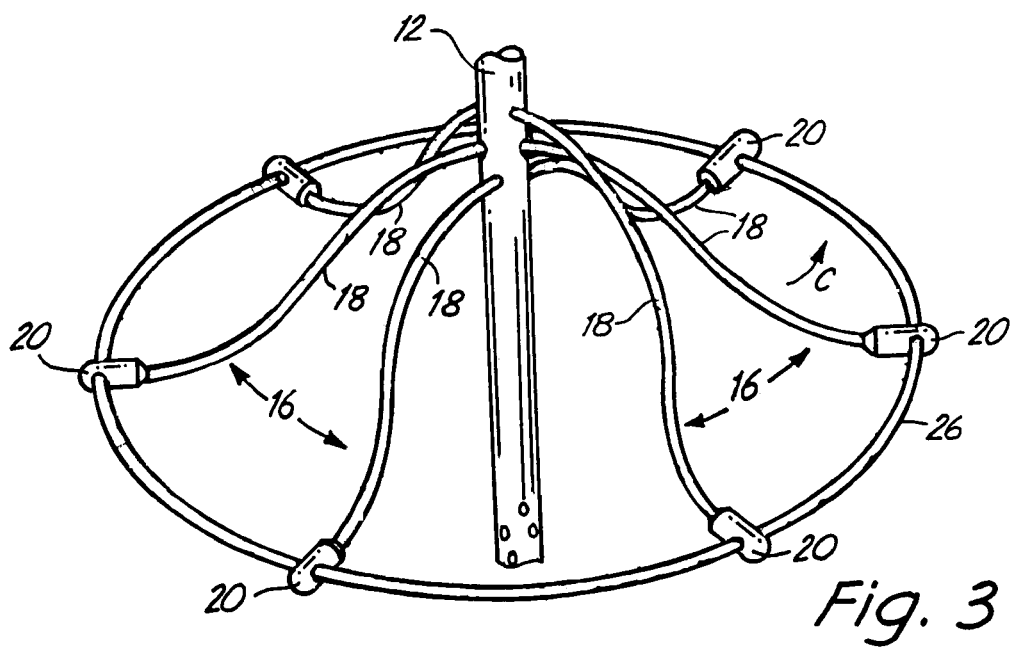
FIG. 3 is a perspective view of the structure of the left side of an occlusion device frame.

FIG. 3 is a perspective view of a portion of the occlusion device 10 shown without the sheets 22, 24 again, for clarity. FIG. 3 illustrates the left side frame of the device to demonstrate how the sets of arms 14, 16 connect to the center post 12 and to the hoop 26. Shown is the center post 12, three wire arms 18, which comprise the left set of arms 16, end caps 20, and a hoop 26. Although FIG. 3 depicts the left side of the device 10, the same construction method applies to the right side of the device 10.

To assemble the device, the arms 18 are threaded through holes drilled through the right portion of the center post 12 to create three sets of arms 16. The end caps 20 are threaded onto the hoop 26 and the ends of the hoop 26 are joined together inside an end cap 20, which is described more fully in FIG. 7A. The ends of the set of arms 16 are then inserted into the end caps 20. Thus, the arms 16 are connected to the hoop 26 via the end caps 20.

The individual wire arms 18 that create the sets of wire arms 14, 16 are shaped to form a self centering portion of the occlusion device. One suitable shape for the arms 18 is a bell shape. This shape allows the device 10 to maintain a low profile once the device 10 is deployed, and also allows the set of arms 16 to center the device 10 within the defect.

After the hoop 26 is threaded through the end caps 20, the arms 18 acquire slight tension, which allows the device 10 to self center in the defect. Before the hoop 26 is added, the arms 18 splay outward and upwards. Once the hoop 26 is added, the arms 18 can no longer splay because the arms 18 are attached to the hoop 16. Tension is created in the arms 18, however, because the arms 18 still have the tendency to splay but cannot because the hoop 26 secures the ends of the arms 18. The tension causes the hoop 26 to be pulled slightly towards the arms 18 and also causes the curved portion of the arms 18 to push outward, away from the center post 12.

When the device 10 is deployed, the tension in the arms 18 allows the device to seal the defect and to center the device 10. As mentioned, the arms 18 slightly pull the hoop 26 toward the arms 18. Once the device 10 is in place, the arms pull the hoop 26 toward the septum so that the defect is sealed. Also, the ends of the set of arms 16 no longer splay out and thus, are compressed slightly to allow the arms 18 to be inserted in the end caps 20 and attached to the hoop 26. In response to the compression, the curved top portion of the set of arms 16 has slight tension. The tension allows the device 10 to self center because, if there is room in the defect for the upper portion of the set of arms to widen, the set of arms 16 widen and expand to accommodate the defect. Because the widening is symmetrical around the center at the device, the device centers itself within the defect.

Figure 4:
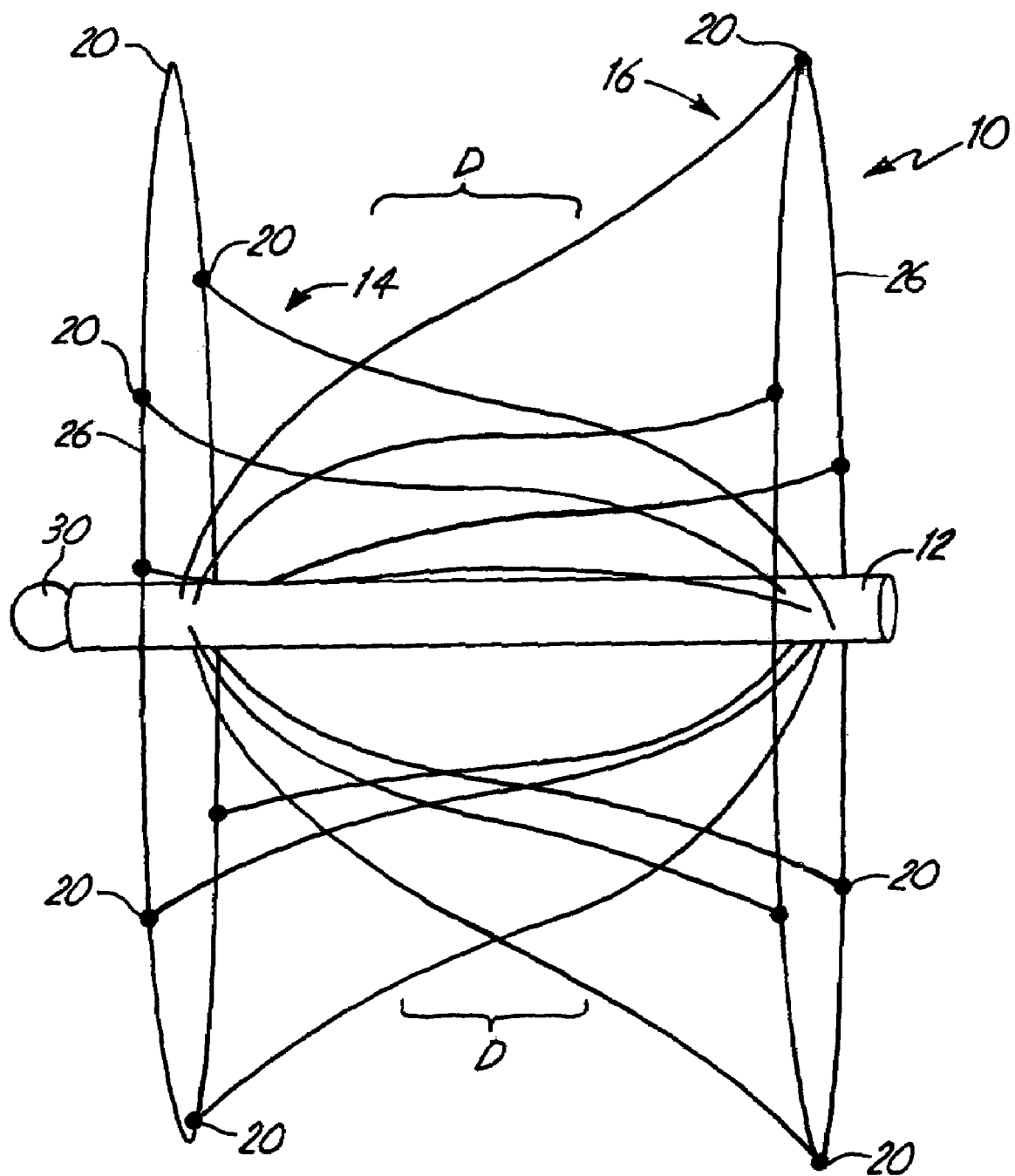
FIG. 4 is a diagrammatic side view of an occlusion device.

FIG. 4 is a diagrammatic side view of the device 10. Shown are hoops 26, sets of arms 14, 16 comprised of individual arms 18, a center post 12, a grasping knob 30, and end caps 20. The set of arms 14, 16 form a flexible intermediate zone D at the device's center. Because the sets 14, 16 are made of wire arms 18 which remain somewhat flexible, the diameter of the zone D adjusts to the size of the defect but does not exert enough force to widen the diameter of the defect. If, however, the defect is large, the set of arms 16 may expand to be the same diameter of the defect and center the device 10 because of the tension mentioned previously.

The size of the device 10 is variable and should correspond to the rough size of the defect so that the device 10 fits the defect properly. The ability of the self centering occlusion device 10 to center itself within the defect is improved when the size of the device 10 is appropriate. If the device 10 is properly sized and centered, the likelihood that the defect will be sealed is increased and the likelihood of blood shunting is reduced.

Figure 5A:
FIG. 5A is a heat shaped wire arm.
Figure 5B:
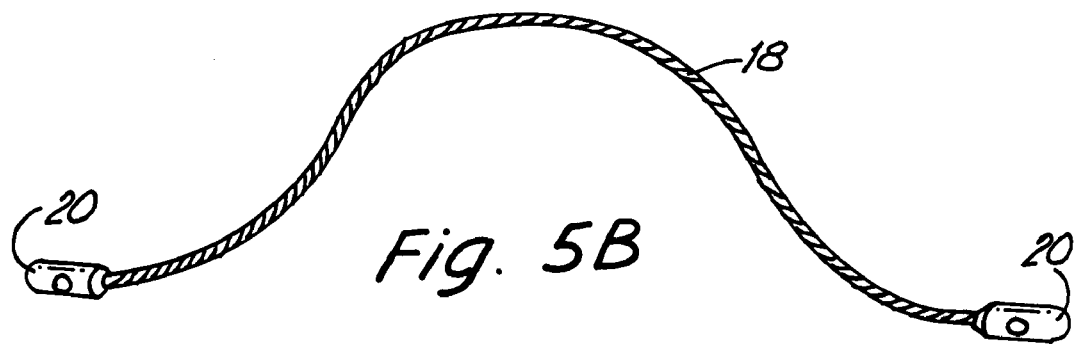
FIG. 5B is a heat shaped stranded cable wire arm.

FIGS. 5A and 5B show a wire arm 18 after it has been heat shaped. In FIG. 5A the wire arm 18 is constructed of a single wire. In FIG. 5B the wire arm is constructed of a stranded cable. Also shown are end caps 20. The wire arm 18 has a bell shape, as mentioned previously. This shape allows the device 10 to maintain a low profile but also exerts enough pressure to cause the device to hug the septum and to center the device. The wire may be heat shaped or shaped by another suitable method. One method of heat shaping the wire is to wrap it around a plate having three cylinders mounted to it. The wire may be wrapped around the cylinders so that it has the appropriate curvature and heated while it remains wrapped around the cylinders. Preferably, the wire is stranded, as in FIG. 5B, to both increase strength and decrease the potential for breakage.

Figure 5C:
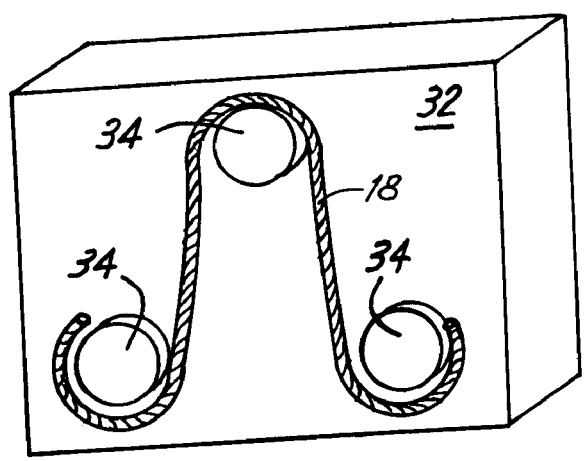
FIG. 5C is a block for heat shaping wire arms.

FIG. 5C demonstrates one method of heat shaping the wire arms 18. Shown is a block 32 having 3 cylinders 34, which are mounted to the block 32, and a wire arm 18. The wire arm 18 is wrapped around the cylinders 34 and then heated. After the wire arm 18 cools, the arm 18 is removed from the block 32 and can then be attached to the device.

Figure 6:
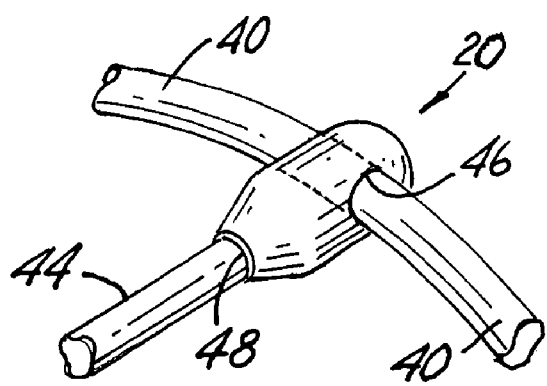
FIG. 6 is a perspective view of an end cap in place on a hoop.

FIG. 6 shows an enlarged perspective view of an end cap 20 in place on a hoop. Shown is an end cap 20, a portion of a support hoop 40, a portion of a wire support arm 44, a hole 46, and an end cavity 48. The support hoop 40 passes through holes 46 drilled crosswise through the end cap 20. The wire support arm 16 is inserted into an end cavity 48 located at the base of the end cap 20.

The end caps 20 cap the wire support arms 18 to protect tissue and prevent unraveling of the wire support arms 18 if the arms 18 are stranded. The tip of the end cap 20 is rounded to reduce the potential for trauma to the tissue surrounding a defect. The end caps 20 also serve as a location for the support hoop 40 and the arms 18 to attach to the occlusion device 10. By providing a link between the wire support arms 18 and the support hoop 40, the end caps 20 assist in providing better distribution of pressure once the device 10 is deployed and exerting pressure on the tissue surrounding a defect.

Figure 7A:
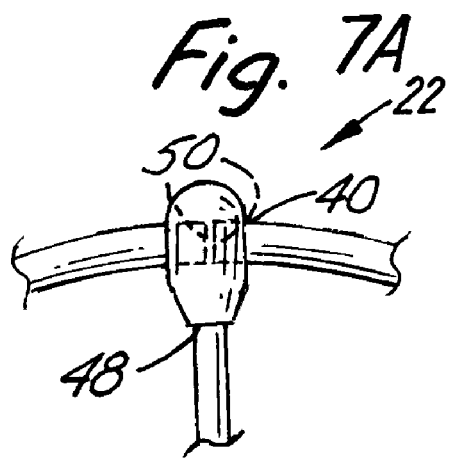
FIG. 7A is a top view of an end cap which demonstrates one method of closing a hoop.
Figure 7B:
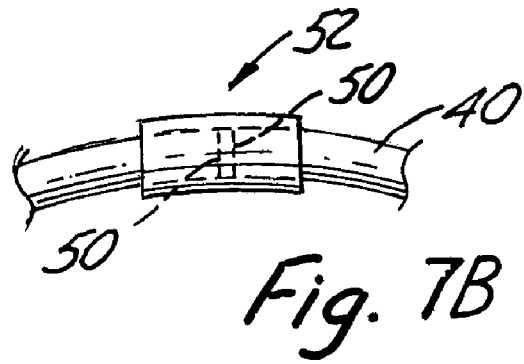
FIG. 7B is a top view of a coupler which demonstrates one method of closing a hoop.

FIGS. 7A and 8B are top plan views of a portion of the support hoop 40. FIGS. 7A and 7B show enlarged views of two examples of how a support hoop 26 can be closed so that it forms a circle. FIG. 7A shows a portion of a support hoop 40 which has been closed inside an end cap 20. Shown is an end cap 20, a portion of a support hoop 40, ends of the support hoop 50, and an end cavity 48.

The support hoop 26 is typically formed of a single wire. To form the hoop 26, the wire must be closed in order to provide a 360° seal around the defect and evenly distribute pressure. The support hoop 26 may be closed after it has been threaded through the end caps 20. In FIG. 7A, the ends of the support hoop 50 meet after passing through holes 46 in the end cap 20 so that the ends 50 are connected inside the end cap 20. The ends of the support hoop 50 are secured in the end cap 20 using any suitable method, such as crimping, welding, or through the use of adhesives. By joining the ends of the support hoop 50 inside an end cap 20, no additional material must be added to the occlusion device 10, thereby keeping the size and weight of the device 10 to a minimum.

FIG. 7B shows a second example of how a support hoop 26 may be closed. FIG. 7B shows a portion of a support hoop 40 which has been closed inside a coupler 52. Shown is a portion of a support hoop 40, ends of the support hoop 50 and a coupler 52. In this example, the coupler 52 is a small hollow tube with a diameter slightly larger than that of the wire used to construct the support hoop 26. The ends of the support hoop 50 are inserted in the coupler 52 where they meet. The coupler 52 can then be crimped or welded so that the ends of the support hoop 50 remain inside the coupler 52.

Other possible methods of joining the ends of the support hoop 50 may include crimping the ends 50 together or welding the ends 50 together without the use of an end cap 20 or coupler 52.

Figure 8:
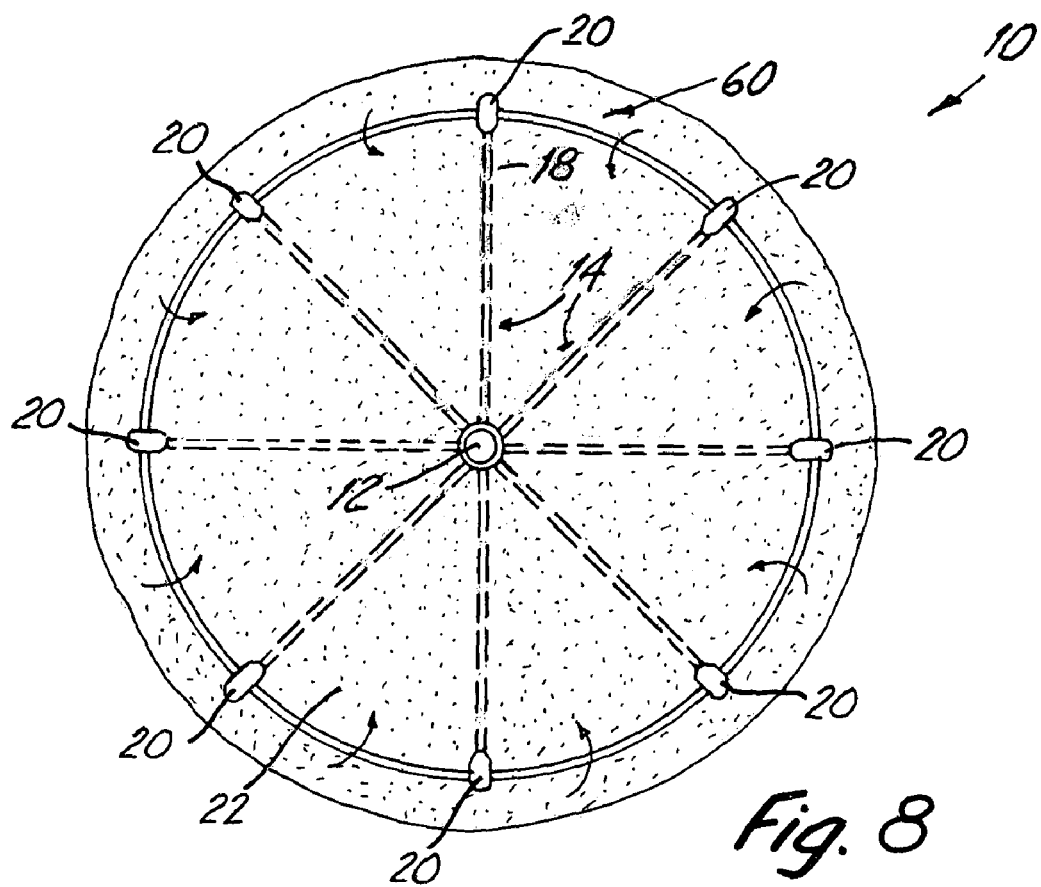
FIG. 8 is a top view of an occlusion device having a hoop which demonstrates how a sail is attached to the support frame and hoop.

FIG. 8 is a top view of an occlusion device 10 which demonstrates how the right and left sheets 22, 24 may be attached to the device 10. Shown is the center post 12, set of arms 14, 16, wire arms 18, end caps 20, the right sheet 20, and the support hoop 26. Also shown is a reinforcement edge 60.

The diameter of the right sheet 20 is slightly larger than that of the support hoop 26. The larger diameter of the sheet 20 extends beyond the support hoop 26 after it is attached to the wire arms 18 and constitutes the reinforcement edge material 60. The reinforcement edge material 60 allows this portion of the sheet to be folded over the support hoop 26 to form a reinforced edge of double material around the perimeter of the device 10. Once the reinforcement edge material 60 has been folded over the support hoop 26, it can be held in place though suturing, bonding, adhesives, heat treating, laminating, or any other suitable method.

Alternatively, the reinforced edge material 60 is created using a separate sheet of foam formed in a ring. The foam ring is sized to allow it to fold over the perimeter of the device 10 and support hoop 26. The foam ring may be attached to the sheet 20 using any suitable method such as suturing, bonding, adhesive, heat treating, or laminating.

Once attached, the reinforcement edge material 60 covers the exposed edges of the occlusion device 10. The reinforcement edge material 60 acts as a cushion between the exposed metal edges of the occlusion device 10 and the tissue surrounding the defect, providing extra protection from pressure that the device 10 exerts on the tissue.

The reinforced edge 60 also secures the sheets 20, 22 to the device 10. Often, in order to adequately seal the defect, the wire arms 18 must bend to accommodate the contours of the heart. Because the sheets 20, 22 are sewn to the wire arms 18, the sheets 20, 22 must accommodate the bending of the wire arms 18. In locations where some of the wire arms 18 are bent by the contours of the heart, a portion of the sheets 20, 22 may be stretched so that it experiences constant tension. This tension may cause the sheets 20, 22 to tear, especially where the sutures 62 are located. If the sheets 20, 22 tear, the sealing ability of the occlusion device 10 may be compromised. The reinforced edge 60 helps to prevent the first and second sheets 20, 22 from tearing at the areas where the sheets 20, 22 are attached to the device 10 or are sutured. Because the reinforcement edge 60 overlaps the hoop 26 and is then affixed to the rest of the sheet 20, 22, it adds an additional 360° of continuous attachment of the sheets 20, 22 to the frame of the device 10 reducing the likelihood of tearing or detachment. The additional foam material along the perimeter of the device helps to distribute the tension on the sheets 20, 22 along a continuum, instead of focusing tension at discrete attachment sites like the suture points.

Figure 9:
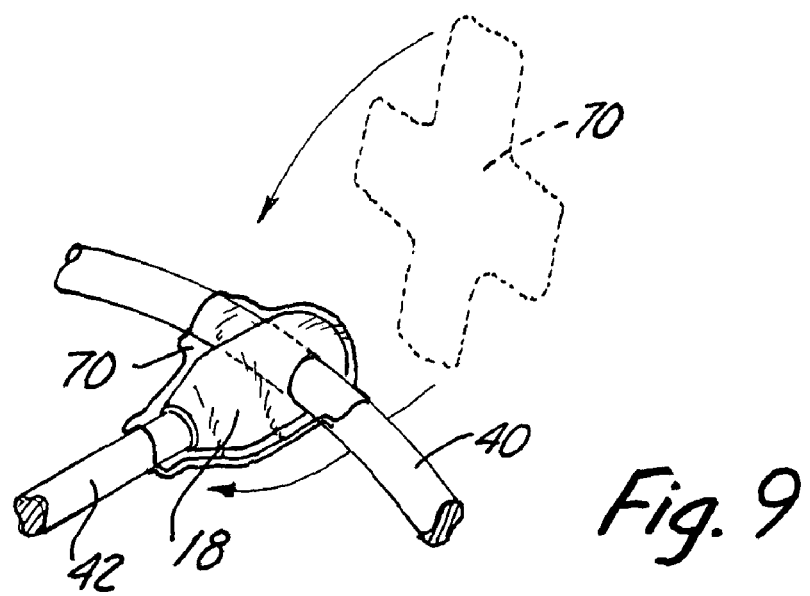
FIG. 9 is a perspective view of a foam patch in place on an occlusion device.

FIG. 9 demonstrates an alternative method of reinforcing attachment of the foam sheets to the occlusion device 10. Shown is a patch 70, a portion of a support hoop 40, a portion of a wire arm 42, and an end cap 22. The patch 70 is constructed of foam and is configured to fit over the end cap 22. In this example, the patch 70 is shaped like a cross which enables it to cover both sides of the end cap 22 and a small portion of the support hoop 40 where the hoop 40 extends out of the end cap 22. The patch 70 may be secured by sutures, heat treatment, laminating, or another suitable method.

In addition to reinforcing the sheets, the patch 70 also acts as a cushion between the metal end caps 22 of the occlusion device 10 and the tissue surrounding the defect, providing extra protection from pressure that the device 10 exerts on the tissue. The patch 70 also reduces the amount of metal to tissue contact.

Although the present invention has been described with reference to preferred embodiments, workers skilled in the art will recognize that changes may be made in form and detail without departing from the spirit and scope of the invention.

The invention claimed is:

1. A self centering occlusion device, the device comprising:
   a center post having a first and second side;
   a first set of arms emanating from the second side of the center post and extending toward the first side;
   a second set of arms emanating from the first side of the center post and extending toward the second side, wherein the first and second sets of arms define a flexible intermediate zone to center the device in an aperture;
   a first sheet attached to the first set of arms adjacent the first side of the center post; and a second sheet attached to the second set of arms adjacent the second side of the center post.

2. The device of claim 1 wherein the arms comprise a bell shape.

3. The device of claim 1 wherein the arms are constructed of stranded wire.

4. The device of claim 1 wherein the sheets are constructed of non-thrombogenic polyvinyl alcohol foam.

5. A self centering occlusion device, the device comprising:
   a center section extending in an axial direction having a distal and proximal end;
   a first sheet located at the distal end of the center section;
   a second sheet located at the proximal end of the center section;
   a first set of arms extending from the proximal end of the center section and attaching to the first sheet;
   a second set of arms extending from the distal end of the center section and attaching to the second sheet;
   a first hoop attached to the first set of arms and the first sheet; and
   a second hoop attached to the second set of arms and the second sheet.

6. The device post of claim 5 wherein the arms comprise a bell shape.

7. The device of claim 5 wherein the arms are constructed of stranded wire.

8. The device of claim 5 wherein the sheets are constructed of non-thrombogenic polyvinyl alcohol foam.

9. An occlusion device for occluding a septal defect, the occlusion device comprising:
   a center post;
   a first occluding body connected to a distal side of the center post;
   a second occluding body connected to a proximal side of the center post;
   a first set of arms emanating from the proximal side of the center post and attaching to the first occluding body;
   a second set of arms emanating from the distal side of the center post and attaching to the second occluding body; and
   wherein the first and second sets of arms form a wire network having a flexible intermediate zone to center the device in an aperture.

10. The device of claim 9 wherein the arms comprise a bell shape.

11. The device of claim 10 wherein the arms are constructed of stranded wire.

12. The device of claim 10 wherein the first and second occluding bodies comprise sheets constructed of polyvinyl alcohol foam.

13. An occlusion device for the closure of a physical anomaly, the device comprising:
   a center post having distal and proximal ends;
   a first set of support arms extending from the proximal end of the center post toward the distal end of the center post;
   a distal sheet attached to the first set of arms adjacent the distal end of the center post;
   a second set of support arms extending from the distal end of the center post toward the proximal end of the center post;
   a proximal sheet attached to the second set of support arms adjacent the proximal end of the center post.

14. The device post of claim 13 wherein the arms comprise a bell shape.

15. The device of claim 13 wherein the arms are constructed of stranded wire.

16. The device of claim 13 wherein the sheets are constructed of non-thrombogenic polyvinyl alcohol foam.

17. An occlusion device, the device comprising:
   a center section having a distal end and a proximal end;
   a proximal sheet located at the proximal end;
   a distal sheet located at the distal end;
   a first set of arms extending from the proximal end of the center section and attaching to the distal sheet; and
   a second set of arms extending from the distal end of the center section and attaching to the proximal sheet.

18. The device of claim 17 wherein the arms comprise a bell shape.

19. The device of claim 17 wherein the arms are constructed of stranded wire.

20. The device of claim 17 wherein the sheets are constructed of polyvinyl alcohol foam.

* * * * *

UNITED STATES PATENT AND TRADEMARK OFFICE
CERTIFICATE OF CORRECTION

| | | |
|---|---|---|
| PATENT NO. | : 7,144,410 B2 | |
| APPLICATION NO. | : 10/666081 | |
| DATED | : December 5, 2006 | |
| INVENTOR(S) | : Joseph A. Marino et al. | |

It is certified that error appears in the above-identified patent and that said Letters Patent is hereby corrected as shown below:

Column 4, Line 30, delete "maybe", insert --may be--

Signed and Sealed this

Twenty-second Day of May, 2007

JON W. DUDAS
*Director of the United States Patent and Trademark Office*